US009540626B2

(12) United States Patent
Lambris et al.

(10) Patent No.: US 9,540,626 B2
(45) Date of Patent: Jan. 10, 2017

(54) REGULATOR OF COMPLEMENT ACTIVATION AND USES THEREOF

(71) Applicant: The Trustees of the University of Pennsylvania, Philadelphia, PA (US)

(72) Inventors: John D. Lambris, Philadelphia, PA (US); Christoph Schmidt, Laugna (DE); Daniel Ricklin, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/386,043

(22) PCT Filed: Mar. 15, 2013

(86) PCT No.: PCT/US2013/032350
§ 371 (c)(1),
(2) Date: Sep. 18, 2014

(87) PCT Pub. No.: WO2013/142362
PCT Pub. Date: Sep. 26, 2013

(65) Prior Publication Data
US 2015/0110766 A1    Apr. 23, 2015

Related U.S. Application Data

(60) Provisional application No. 61/612,512, filed on Mar. 19, 2012.

(51) Int. Cl.
| | | |
|---|---|---|
| *C12N 9/88* | (2006.01) | |
| *C07K 14/47* | (2006.01) | |
| *A61K 38/51* | (2006.01) | |
| *A61K 38/00* | (2006.01) | |

(52) U.S. Cl.
CPC .............. *C12N 9/88* (2013.01); *A61K 38/51* (2013.01); *C07K 14/472* (2013.01); *A61K 38/00* (2013.01); *C12Y 402/01002* (2013.01)

(58) Field of Classification Search
CPC ................................. C12N 9/88; C07K 14/472
See application file for complete search history.

(56) References Cited

FOREIGN PATENT DOCUMENTS

| WO | WO 9823638 | 7/1998 |
|---|---|---|
| WO | WO 2007056227 A2 | 10/2007 |
| WO | WO 2010034015 A2 | 7/2010 |
| WO | WO 2011107591 A1 | 9/2011 |
| WO | WO 2011113641 A1 | 9/2011 |

OTHER PUBLICATIONS

Ferreira et al. 2010; Complement control protein factor H: the good, the bad, and the inadequate. Molecular Immunology. 47: 2187-2197.*

Sharma et al. 1996; Identification of three physically and functional distinct binding cites for C3b in human complement factor H by deletion mutagenesis. Proc. Natl. Acad. Sci. 93: 10996-11001.*

Alcorlo, M., et al. "Unique structure of iC3b resolved at a resolution of 24 Å by 3D-electron microscopy" Proc. Natl. Acad. Sci. 108(32) (2011): 13236-40.

Aslam, M. and Perkins, S.J. "Folded-back solution structure of monomeric factor H of human complement by synchrotron X-ray and neutron scattering, analytical ultracentrifugation and constrained molecular modeling" J. Mol. Biol. 309 (2001): 1117-1138.

De Cordoba, S.R. and De Jorge, E.G. Translational mini-review series on complement factor H: genetics and disease associations of human complement factor H. Clin. and Exp. Immunol. 151 (2008): 1-13.

Fridkis-Hareli, M., et al. "Design and development of TT30, a novel C3d-targeted C3/C5 convertase inhibitor for treatment of human complement alternative pathway-mediated diseases" Blood. 118 (2001): 4705-4713.

Hebecker, M., et al. "An engineered construct combining complement regulatory and surface-recognition domains represents a minimal-size functional factor H" J. of Immunol. 191 (2013): 912-921.

Holers, V.M. "The spectrum of complement alternative pathway-mediated diseases" Immunol. Rev. 233 (2008): 300-316.

Jozsi, M. and Zipfel, P.F. Trends Immunol. "Factor H family proteins and human diseases" 29 (2008): 380-387.

Meri, S. "Loss of self-control in the complement system and innate autoreactivity" Ann N Y Acad Sci. 109 (2007): 93-105.

Morgan, H.P., et al. "Structural basis for engagement by complement factor H of C3b on a self surface" Nature Structural and Molecular Biology. 18(4) (2011): 463-470.

Opperman, M., et al. "The C-terminus of complement regulator Factor H mediates target recognition: evidence for a compact conformation of the native protein" Clin. and Exp. Immunol. 144 (2006): 342-352.

Pickering, M.C. and Cook, H.T. "Translational mini-review series on complement H: renal diseases associated with complement factor H: novel insights from humans and animals" Clin. and Exp. Immunol. 151 (2008): 210-230.

Ripoche, J., et al. "The complete amino acid sequence of human complement factor H" Biochem. J. 249 (1988): 593-602.

Risitano, A.M., et al. "C3-Mediated Extravascular Hemolysis in Paroxysmal Nocturnal Hemoglobinuria: An In Vitro Model to Dissect Complement C3 Activation Comparing . . . " Blood (ASH Annual Meeting Abstracts). 116 (2010): Abstract 637.

(Continued)

*Primary Examiner* — Karen Cochrane Carlson
(74) *Attorney, Agent, or Firm* — Potter Anderson and Corroon, LLP

(57) ABSTRACT

A potent complement regulator is disclosed. The complement regulator comprises a complement regulatory region connected by a flexible linker to a multifunctional binding region that enables binding to C3b activation/inactivation products and/or oxidation end products, as well as to polyanionic surface markers on host cells. An embodiment of the invention utilizes factor H SCRs 1-4 as the complement regulatory region and factor H SCRs 19 and 20 as the multifunctional binding region, linked together by a poly-Gly linker at least 12 residues in length. Pharmaceutical compositions comprising the complement regulator and methods of using the complement regulator are also disclosed.

19 Claims, 6 Drawing Sheets

(56) References Cited

OTHER PUBLICATIONS

Rohrer, B., et al. "A targeted inhibitor of the alternative complement pathway reduces angiogenesis in a mouse model of age-related macular degeneration" Investigative Opthalmology & Visual Science. 50(7) (2009): 3056-3064.
Ross, G.D., et al. "Generation of three different fragments of bound C3 with purified factor I or serum: I. Requirements for factor H vs CR1 cofactor activity" J. of Immunol. 129(5) (1982): 1295-2051.
Ross, G.D., et al. "Generation of three different fragments of bound C3 with purified factor I or serum: II. Location of binding sites in the C3 fragments for factors B and H, complement receptors, and bovine conglutinin" J. Exp. Med. 158 (1983) 334-352.
Schmidt, C.Q., et al. "The central portion of factor H (modules 10-15) is compact and contains a structurally deviant CCP module" J. Mol. Biol. 395 (2010): 105-122.
Schmidt, C.Q., et al. "A new map of glycosaminoglycan and C3b binding sites of factor H" J. of Immunol. 181 (2008): 2610-2619.
Schmidt, C.Q., et al. "Rational engineering of a minimized immune inhibitor with unique triple-targeting properties" J. of Immunol. 190 (2013): 5715-5721.
Weismann, D., et al. "Complement factor H binds malondialdehyde epitopes and protects from oxidative stress" Nature. 478 (2011): 76-81.
Wu, J., et al. "Structure of complement fragment C3b-factor H and implications for host protection by complement regulators" Nature Immunol. 10(7) (2009) 728-733.
International Search Report and Written Opinion for PCT/US2013/032350 (mailed Aug. 7, 2013).

\* cited by examiner

```
                                 SCR 1----------------------------------------------------------->
1     MRLLAKIICL MLWAICVAED CNELPPRRNT EILTGSWSDQ TYPEGTQAIY KCRPGYRSLG
                        ED CNELPPRRNT EILTGSWSDQ TYPEGTQAIY KCRPGYRSLG

------------------/     SCR 2-------------------------------------------------->
61    NVIMVCRKGE WVALNPLRKC QKRPCGHPGD TPFGTFTLTG GNVFEYGVKA VYTCNEGYQL
      NIIMVCRKGE WVALNPLRKC QKRPCGHPGD TPFGTFTLTG GNVFEYGVKA VYTCNEGYQL

------------------/    SCR 3--------------------------------------------------->
121   LGEINYRECD TDGWTNDIPI CEVVKCLPVT APENGKIVSS AMEPDREYHF GQAVRFVCNS
      LGEINYRECD TDGWTNDIPI CEVVKCLPVT APENGKIVSS AMEPDREYHF GQAVRFVCNS

------------------------/     SCR 4------------------------------------------->
181   GYKIEGDEEM HCSDDGFWSK EKPKCVEISC KSPDVINGSP ISQKIIYKEN ERFQYKCNMG
      GYKIEGDEEM HCSDDGFWSK EKPKCVEISC KSPDVINGSP ISQKIIYKEN ERFQYKCNMG

-----------------------/
241   YEYSERGDAV CTESGWRPLP SCEEKSCDNP YIPNGDYSPL RIKHRTGDEI TYQCRNGFYP
      YEYSERGDAV CTESGWRPLP SCEEA          [GGGGGGGGGGGG]

301   ATRGNTAKCT STGWIPAPRC TLKPCDYPDI KHGGLYHENM RRPYFPVAVG KYYSYYCDEH
361   FETPSGSYWD HIHCTQDGWS PAVPCLRKCY FPYLENGYNQ NHGRKFVQGK SIDVACHPGY
421   ALPKAQTTVT CMENGWSPTP RCIRVKTCSK SSIDIENGFI SESQYTYALK EKAKYQCKLG
481   YVTADGETSG SIRCGKDGWS AQPTCIKSCD IPVFMNARTK NDFTWFKLND TLDYECHDGY
541   ESNTGSTTGS IVCGYNGWSD LPICYERECE LPKIDVHLVP DRKKDQYKVG EVLKFSCKPG
601   FTIVGPNSVQ CYHFGLSPDL PICKEQVQSC GPPPELLNGN VKEKTKEEYG HSEVVEYYCN
661   PRFLMKGPNK IQCVDGEWTT LPVCIVEEST CGDIPELEHG WAQLSSPPYY YGDSVEFNCS
721   ESFTMIGHRS ITCIHGVWTQ LPQCVAIDKL KKCKSSNLII LEEHLKNKKE FDHNSNIRYR
781   CRGKEGWIHT VCINGRWDPE VNCSMAQIQL CPPPPQIPNS HNMTTTLNYR DGEKVSVLCQ
841   ENYLIQEGEE ITCKDGRWQS IPLCVEKIPC SQPPQIEHGT INSSRSSQES YAHGTKLSYT
901   CEGGFRISEE NETTCYMGKW SSPPQCEGLP CKSPPEISHG VVAHMSDSYQ YGEEVTYKCF
961   EGFGIDGPAI AKCLGEKWSH PPSCIKTDCL SLPSFENAIP MGEKKDVYKA GEQVTYTCAT
1021  YYKMDGASNV TCINSRWTGR PTCRDTSCVN PPTVQNAYIV SRQMSKYPSG ERVRYQCRSP

SCR 19------------------------------------>
1081  YEMFGDEEVM CLNGNWTEPP QCKDSTGKCG PPPPIDNGDI TSFPLSVYAP ASSVEYQCQN
                                 GKCG PPPPIDNGDI TSFPLSVYAP ASSVEYQCQN

----------------------------/    SCR 20--------------------------------------->
1141  LYQLEGNKRI TCRNGQWSEP PKCLHPCVIS REIMENYNIA LRWTAKQKLY SRTGESVEFV
      LYQLEGNKRI TCRNGQWSEP PKCLHPCVIS REIMENYNIA LRWTAKQKLY SRTGESVEFV

-----------------------------------/
1201  CKRGYRLSSR SHTLRTTCWD GKLEYPTCAK R
      CKRGYRLSSR SHTLRTTCWD GKLEYPTCAK R
```

FIG. 2

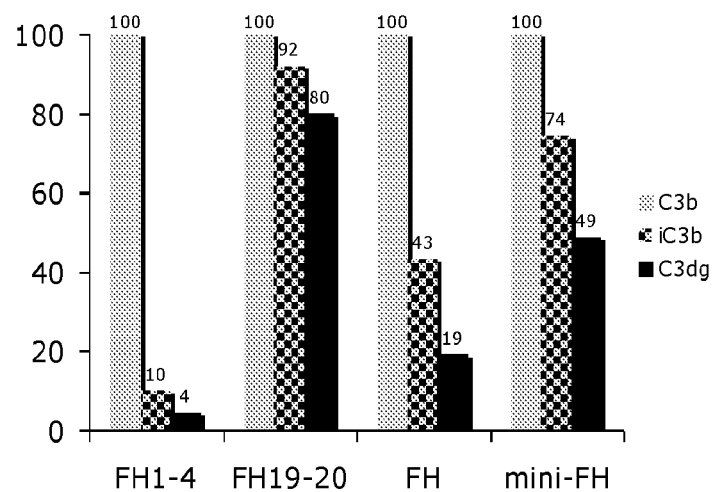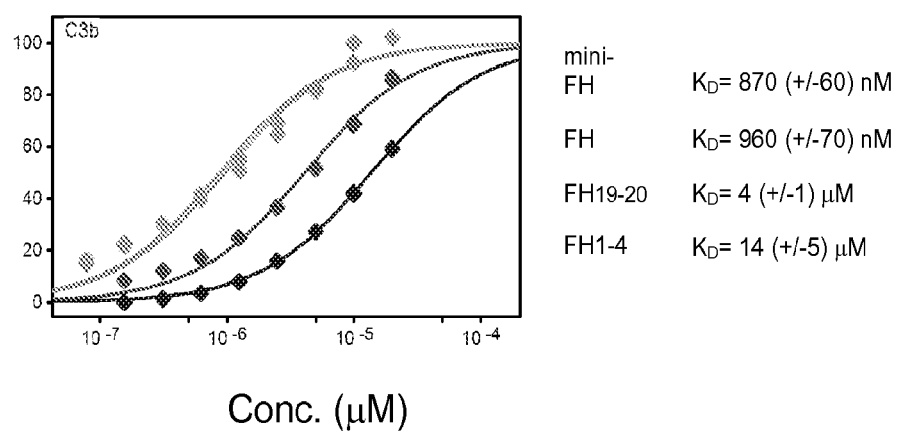
FIG. 4

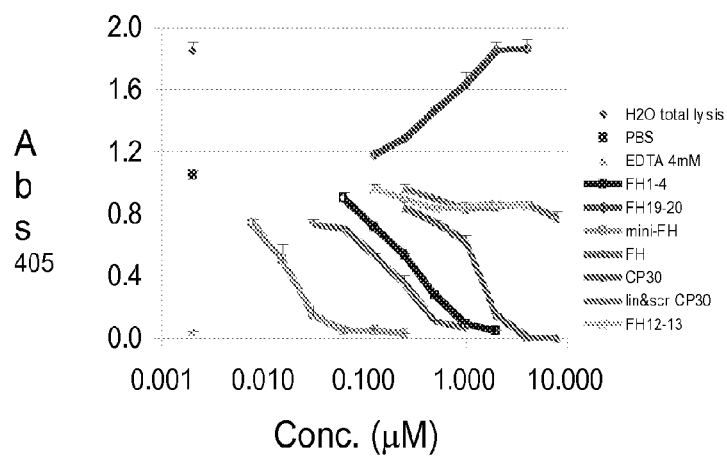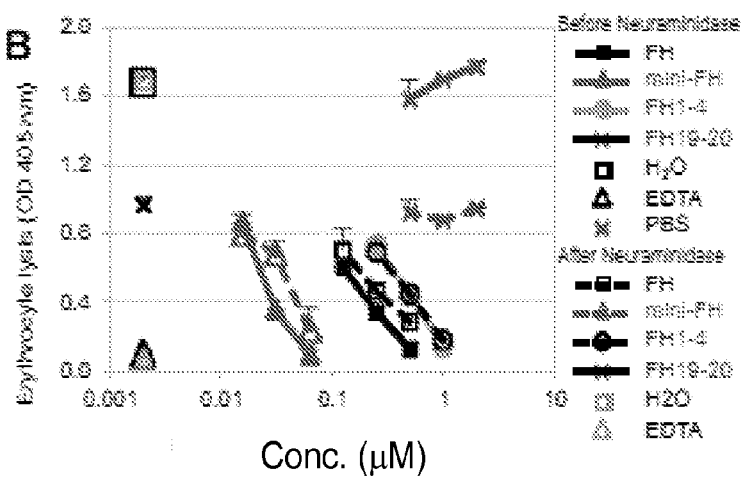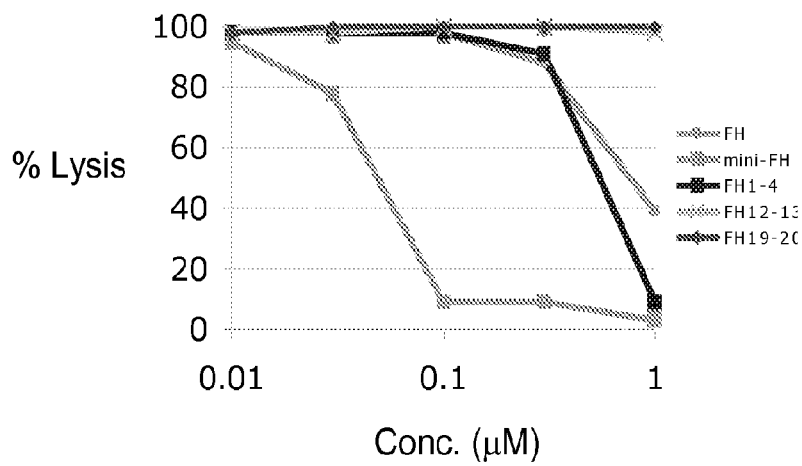
FIG. 6

ID BY REFERENCE

SEQUENCE LISTING

<160> NUMBER OF SEQ ID NOS: 3

<210> SEQ ID NO 1
<211> LENGTH: 1231
<212> TYPE: PRT
<213> ORGANISM: Homo sapiens

<400> SEQUENCE: 1

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
```

```
                     85                  90                  95
Thr Leu Thr Gly Gly Asn Val Phe Glu Tyr Gly Val Lys Ala Val Tyr
            100                 105                 110
Thr Cys Asn Glu Gly Tyr Gln Leu Leu Gly Glu Ile Asn Tyr Arg Glu
            115                 120                 125
Cys Asp Thr Asp Gly Trp Thr Asn Asp Ile Pro Ile Cys Glu Val Val
130                 135                 140
Lys Cys Leu Pro Val Thr Ala Pro Glu Asn Gly Lys Ile Val Ser Ser
145                 150                 155                 160
Ala Met Glu Pro Asp Arg Glu Tyr His Phe Gly Gln Ala Val Arg Phe
            165                 170                 175
Val Cys Asn Ser Gly Tyr Lys Ile Glu Gly Asp Glu Glu Met His Cys
            180                 185                 190
Ser Asp Asp Gly Phe Trp Ser Lys Glu Lys Pro Lys Cys Val Glu Ile
            195                 200                 205
Ser Cys Lys Ser Pro Asp Val Ile Asn Gly Ser Pro Ile Ser Gln Lys
    210                 215                 220
Ile Ile Tyr Lys Glu Asn Glu Arg Phe Gln Tyr Lys Cys Asn Met Gly
225                 230                 235                 240
Tyr Glu Tyr Ser Glu Arg Gly Asp Ala Val Cys Thr Glu Ser Gly Trp
            245                 250                 255
Arg Pro Leu Pro Ser Cys Glu Glu Lys Ser Cys Asp Asn Pro Tyr Ile
            260                 265                 270
Pro Asn Gly Asp Tyr Ser Pro Leu Arg Ile Lys His Arg Thr Gly Asp
        275                 280                 285
Glu Ile Thr Tyr Gln Cys Arg Asn Gly Phe Tyr Pro Ala Thr Arg Gly
    290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
            325                 330                 335
His Glu Asn Met Arg Arg Pro Tyr Phe Pro Val Ala Val Gly Lys Tyr
            340                 345                 350
Tyr Ser Tyr Tyr Cys Asp Glu His Phe Glu Thr Pro Ser Gly Ser Tyr
        355                 360                 365
Trp Asp His Ile His Cys Thr Gln Asp Gly Trp Ser Pro Ala Val Pro
        370                 375                 380
Cys Leu Arg Lys Cys Tyr Phe Pro Tyr Leu Glu Asn Gly Tyr Asn Gln
385                 390                 395                 400
Asn His Gly Arg Lys Phe Val Gln Gly Lys Ser Ile Asp Val Ala Cys
            405                 410                 415
His Pro Gly Tyr Ala Leu Pro Lys Ala Gln Thr Thr Val Thr Cys Met
            420                 425                 430
Glu Asn Gly Trp Ser Pro Thr Pro Arg Cys Ile Arg Val Lys Thr Cys
            435                 440                 445
Ser Lys Ser Ser Ile Asp Ile Glu Asn Gly Phe Ile Ser Glu Ser Gln
    450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Arg Cys Gly Lys
            485                 490                 495
Asp Gly Trp Ser Ala Gln Pro Thr Cys Ile Lys Ser Cys Asp Ile Pro
            500                 505                 510
```

```
Val Phe Met Asn Ala Arg Thr Lys Asn Asp Phe Thr Trp Phe Lys Leu
            515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
            595                 600                 605

Val Gln Cys Tyr His Phe Gly Leu Ser Pro Asp Leu Pro Ile Cys Lys
            610                 615                 620

Glu Gln Val Gln Ser Cys Gly Pro Pro Glu Leu Leu Asn Gly Asn
625                 630                 635                 640

Val Lys Glu Lys Thr Lys Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
            690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
            770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
            885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
            915                 920                 925
```

```
Leu Pro Cys Lys Ser Pro Pro Glu Ile Ser His Gly Val Val Ala His
930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
                980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 2
<211> LENGTH: 384
<212> TYPE: PRT
<213> ORGANISM: Artificial Sequence
<220> FEATURE:
<223> OTHER INFORMATION: mini-FH
<220> FEATURE:
<221> NAME/KEY: MISC_FEATURE
<222> LOCATION: (248)..(259)
<223> OTHER INFORMATION: poly-glycine linker

<400> SEQUENCE: 2

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
                20                  25                  30
```

```
Lys Cys Arg Pro Gly Tyr Arg Ser Leu Gly Asn Ile Ile Met Val Cys
         35                  40                  45

Arg Lys Gly Glu Trp Val Ala Leu Asn Pro Leu Arg Lys Cys Gln Lys
     50                  55                  60

Arg Pro Cys Gly His Pro Gly Asp Thr Pro Phe Gly Thr Phe Thr Leu
 65              70                  75                      80

Thr Gly Gly Asn Val Phe Glu Tyr Gly Val Lys Ala Val Tyr Thr Cys
                 85                  90                  95

Asn Glu Gly Tyr Gln Leu Leu Gly Glu Ile Asn Tyr Arg Glu Cys Asp
                100                 105                 110

Thr Asp Gly Trp Thr Asn Asp Ile Pro Ile Cys Glu Val Val Lys Cys
            115                 120                 125

Leu Pro Val Thr Ala Pro Glu Asn Gly Lys Ile Val Ser Ser Ala Met
        130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
            195                 200                 205

Tyr Lys Glu Asn Glu Arg Phe Gln Tyr Lys Cys Asn Met Gly Tyr Glu
        210                 215                 220

Tyr Ser Glu Arg Gly Asp Ala Val Cys Thr Glu Ser Gly Trp Arg Pro
225                 230                 235                 240

Leu Pro Ser Cys Glu Glu Ala Gly Gly Gly Gly Gly Gly Gly Gly Gly
                245                 250                 255

Gly Gly Gly Gly Lys Cys Gly Pro Pro Pro Ile Asp Asn Gly Asp
                260                 265                 270

Ile Thr Ser Phe Pro Leu Ser Val Tyr Ala Pro Ala Ser Ser Val Glu
            275                 280                 285

Tyr Gln Cys Gln Asn Leu Tyr Gln Leu Glu Gly Asn Lys Arg Ile Thr
        290                 295                 300

Cys Arg Asn Gly Gln Trp Ser Glu Pro Pro Lys Cys Leu His Pro Cys
305                 310                 315                 320

Val Ile Ser Arg Glu Ile Met Glu Asn Tyr Asn Ile Ala Leu Arg Trp
                325                 330                 335

Thr Ala Lys Gln Lys Leu Tyr Ser Arg Thr Gly Glu Ser Val Glu Phe
            340                 345                 350

Val Cys Lys Arg Gly Tyr Arg Leu Ser Ser Arg Ser His Thr Leu Arg
        355                 360                 365

Thr Thr Cys Trp Asp Gly Lys Leu Glu Tyr Pro Thr Cys Ala Lys Arg
    370                 375                 380

<210> SEQ ID NO 3
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: n-methyl-glycine
<220> FEATURE:
```

```
-continued

<221> NAME/KEY: DISULFID
<222> LOCATION: (3)..(13)
<223> OTHER INFORMATION: Cysteines joined via disulfide bridge
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: n-methyl-glycine
<220> FEATURE:
<221> NAME/KEY: MOD_RES
<222> LOCATION: (14)..(14)
<223> OTHER INFORMATION: n-methyl-isoleusine
<220> FEATURE:
<221> NAME/KEY: MOD_RES
<222> LOCATION: (14)..(14)
<223> OTHER INFORMATION: AMIDATION

<400> SEQUENCE: 3

Gly Ile Cys Val Trp Gln Asp Trp Gly Ala His Arg Cys Ile
1               5                   10
```

REGULATOR OF COMPLEMENT ACTIVATION AND USES THEREOF

This is a U.S. national filing, pursuant to 35 U.S.C. §371, of International Application No. PCT/US2013/032350, filed Mar. 15, 2013, which claims benefit of U.S. Provisional Application No. 61/612,512, filed Mar. 19, 2012, the entire contents of each of which are incorporated by reference herein.

This invention was made with government support under Grant Nos. GM62134 and AI068730 awarded by the National Institutes of Health. The government has certain rights in the invention.

FIELD OF THE INVENTION

This invention relates to the field of the innate immune system and complement activation. In particular, the invention provides regulators of complement activation, particularly via the alternative pathway, comprising a complement regulatory region connected by a flexible linker to a multifunctional binding region that enables binding to C3b activation/inactivation products and/or oxidation end products, as well as to polyanionic surface markers on host cells.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

The efficacy of the complement-mediated immune response relies on a delicate balance between activation and regulation. Although continuous generation of the strong opsonin complement fragment C3b by the alternative pathway (AP) allows rapid reaction to foreign or abnormal cells, its indiscriminate deposition may potentially cause host tissue damage. Host cells are therefore protected by proteins of the regulator of complement activation (RCA) family, which either impair the generation of new C3b by accelerating the decay of the C3 convertases or act as cofactor for factor 1 (F1) in degrading existing C3b. In addition to cell surface-bound RCA proteins such as decay accelerating factor (DAF (A000571); also called CD55), membrane cofactor protein (MCP (A000568); also called CD46) and complement receptor 1 (CR1; also called CD35), the soluble and highly abundant regulator factor H (FH) offers an additional layer of protection, as it controls the steady-state alternative pathway activation in circulation and on surfaces to which it specifically binds.

Factor H, the second most abundant complement protein in plasma, is the primary regulator of the AP. It is a large (155 kDa), soluble glycoprotein that circulates in human plasma. It has an elongated structure consisting of 20 homologous short consensus repeats (SCR, also referred to as complement control protein (CCP) domains or modules), each comprising approximately 60 residues that are common to all RCA proteins (Schmidt C Q et al., 2008, *Clin Exp Immunol* 151: 14-24), held together by four conserved cysteine residues. Whereas the complement regulatory functions are concentrated to the N-terminus (SCR 1-4) of factor H, two distinct regions (SCR 6-8, SCR 19-20) define the recognition of self-surfaces via binding to polyanion patches (e.g., glycosaminoglycans; GAG) on host cells. Factor H regulates the AP by inhibiting the formation of the AP C3 convertase and accelerating its dissociation, or by acting as cofactor for the degradation of C3b by factor I (Wu, J et al., 2009, *Nat Immunol* 10:728-733; Schmidt, C et al., 2008, *J Immunol* 181:2610-2619; Schmidt, C et al., 2008, *Clin Exp Immunol* 151:14-24; Pickering, M C et al., 2008, *Clin Exp Immunol* 151:210-230; Jozsi, M, & P F Zipfel, 2008, *Trends Immunol* 29:380-387; Ross, G D et al., 1982, *J Immunol* 129:2051-2060).

Though a soluble protein, FH may be recruited to host membranes by recognizing and binding self-components, such as glycosaminoglycans, and thereby may prevent the opsonization of host tissue with low surface expression of RCA. The importance of FH in maintaining a well-balanced immune response is reflected by the increasing number of diseases found to have strong association with mutations and polymorphisms in the gene encoding FH, as found in age-related macular degeneration (AMD), atypical hemolytic uremic syndrome (aHUS) and membrano-proliferative glomerulonephritis type II (MPGN-II) (Meri, S, 2007, *Ann NY Acad Sci* 1109: 93-105; de Cordoba, S R & de Jorge, E G, 2008, *Clin Exp Immunol* 151: 1-13). Because of their vital function in immune modulation, therapeutic targeting of FH and other RCA proteins has been considered important for the treatment of diseases associated with abnormal or loss of complement control.

In accordance with a current model of FH engagement of C3b on a self-surface, concurrent recognition of C3b-opsonins and host-surface markers enable FH to control complement activation effectively on self, but not on foreign surfaces. This specificity depends on the simultaneous binding of FH19-20 to the thioester domain (TED or C3d domain) of C3b, and to polyanions. Proteolytic cleavage within the complement C1r/C1s, Uegf, Bmp1 (CUB) domain of C3b inactivates C3b and yields iC3b (inactive C3b). With proteolysis of CUB, C3b loses one interaction patch for the N-terminal FH domains (Wu J et al., 2009 *Nat Immunol* 10: 728-733; Schmidt C Q et al., 2008, *J Immunol* 181: 2610-2619), but iC3b still contains TED, the interaction partner of C-terminal domains 19-20 of FH. Even so, FH no longer binds readily to iC3b under physiological conditions, irrespective of iC3b being positioned on a cell surface (Ross G D et al., 1983, *J Exp Med* 158: 334-352) or directly on a biosensor (Alcorlo M et al., 2011, *Proc Natl Acad Sci USA* 108: 13236-13240). In contrast, FH19-20 binds indiscriminately well to the TED of C3b, C3dg and C3d (Morgan H P et al., 2011, *Nat Struct Mol Biol* 18, 463-470).

A role of FH in abatement of oxidative stress was established recently. Malondialdehyde (MDA) is a common lipid peroxidation product that accumulates in many pathological processes, including AMD. FH has been identified as a major MDA-binding protein that can block both the uptake of MDA-modified proteins by macrophages and MDA-induced proinflammatory effects in vivo in mice (Weismann D et al., 2011, *Nature* 478: 76-81). SCRs 7 and 20 were demonstrated to mediate the binding of FH to MDA (Id.).

The AP has been shown to play a particularly important role in preclinical disease models and by studies of human diseases, where mutations or dysfunctional polymorphisms that promote activation of the AP are highly associated with diseases such as aHUS, dense deposit disease, AMD and paroxysmal nocturnal hemoglobinuria (PNH) (see Holers, V M, 2008, *Immunol Rev* 223: 300-316). Diseases in which a primary pathogenic role for the alternative pathway has been shown or postulated in or from preclinical studies in animals include rheumatoid arthritis (RA), systemic lupus erythematosus (SLE), several autoimmune and autoinflammatory kidney diseases, autoimmune myocarditis, multiple sclerosis, traumatic brain and spinal cord injury, intestinal and renal ischemia-reperfusion (IR) injury, spontaneous and recurrent pregnancy loss, anti-phospholipid syndrome (APS), asthma, anti-nuclear cytoplasmic antigen-associated pauci-immune vasculitis (Wegener's syndrome), non-lupus autoimmune skin diseases such as pemphigus, bullous pemphigoid, and epidermolysis bullosa, post-traumatic shock and atherosclerosis (Holers, 2008, supra).

A milestone in complement intervention strategies was marked by the approval of the humanized monoclonal antibody Eculizumab for the treatment of the orphan diseases PNH and aHUS. Both diseases are characterized by malfunctioning of complement regulators and result in insufficient control of the AP. Eculizumab binds C5 and inhibits its activation into C5a, a potent anaphylatoxin, and C5b, the initiator of the terminal pathway, and consequently inhibits inflammatory signaling and cell lysis by MAC. However, use of Eculizumab can be disadvantageous; for instance, its use increases susceptibility to infections. Additionally, Eculizumab treatment costs are extremely high and an appreciable proportion of PNH patients do not respond to Eculizumab treatment. These disadvantages have boosted the preclinical development of the chimeric fusion protein TT30, which intervenes earlier in the complement cascade at C3-level, is AP-specific and targets to sites of C3-inactivation products predominantly found on host surfaces (Fridkis-Hareli M, et al., 2011, *Blood* 118: 4705-4713).

From the foregoing discussion, it is clear that improved regulators of the AP of complement activation are needed. The present invention satisfies that need.

SUMMARY OF THE INVENTION

One aspect of the present invention features a complement regulator comprising a complement regulating region that includes a plurality of complement control proteins (CCPs), linked by a flexible linker to a multifunctional binding region that enables binding of the complement regulator to one or more C3b activation/inactivation products, one or more oxidation end products and/or one or more polyanionic surface markers on host cells. The complement regulator at least regulates AP-mediated complement activation. In one embodiment, the C3b activation/inactivation products to which the complement regulators bind contain thioester domains (TEDs). These include C3b, iC3b, C3dg and C3d. The polyanionic surface markers on host cells to which the complement regulators bind include N-linked glycosyl units with sialic acid end-groups or glycosaminoglycans (GAGs) selected from heparin, heparan sulfate, chondroitin sulfate, dermantan sulfate, keratan sulfate and hyaluronan. The oxidation end products to which the complement regulators bind include malondialdehyde (MDA), 4-hydroxynonenal (4-HNE), carboxyethylpyrrole (CEP), oxidized phosphatidylserine (OxPS), oxidized cardiolipin (OxCL) and phosphocholine (PC).

In one embodiment, the CCPs of the complement regulatory region and/or the multifunctional binding region are derived from factor H. In particular, the CCPs of the complement regulatory region are derived from SCRs 1-4 of factor H. In one embodiment, the multifunctional binding region is derived from SCRs 19 and 20 of factor H. In certain embodiments, the linker that links the complement regulatory region to the multifunctional binding region is of the same length and flexibility as a poly-Gly peptide at least 10, 11 or 12 residues in length. In particular, the linker is a poly-Gly peptide at least 12 residues in length.

In one embodiment, the aforementioned complement regulator comprises, from N- to C-terminus, SCRs 1-4 of factor H, a poly-Gly linker at least 12 residues in length, and SCRs 19-20 of factor H. The factor H is human factor H in certain embodiments. In particular the factor H comprises a polypeptide that is functionally equivalent to SEQ ID NO:2. That polypeptide typically comprises a sequence that is more than 90% identical to that of SEQ ID NO:2. An exemplary embodiment of the complement regulator comprises SEQ ID NO:2.

Another aspect of the invention features a polypeptide comprising, from N- to C-terminus, SCRs 1-4 of factor H, a poly-Gly linker at least 12 residues in length, and SCRs 19-20 of factor H. In one embodiment, the factor H is human factor H. In a particular embodiment, the polypeptide comprises SEQ ID NO:2.

Another aspect of the invention features a pharmaceutical composition that includes a pharmaceutically acceptable carrier and a complement regulator complement regulating region that includes a plurality of complement control proteins (CCPs), linked by a flexible linker to a multifunctional binding region that enables binding of the complement regulator to one or more C3b activation/inactivation products, one or more oxidation end products and/or one or more polyanionic surface markers on host cells. The complement regulator in the pharmaceutical composition regulates AP-mediated complement activation.

Another aspect of the invention features a method of regulating complement activation comprising contacting a medium in which regulation of complement activation is desired with a complement regulator comprising a complement regulating region that includes a plurality of complement control proteins (CCPs), linked by a flexible linker to a multifunctional binding region that enables binding of the complement regulator to one or more C3b activation/inactivation products, one or more oxidation end products and/or one or more polyanionic surface markers on host cells, wherein the contacting results in regulation of complement activation in the medium. In one embodiment, the method comprises regulation of AP-mediated complement activation. In one embodiment, the medium includes cells or tissues of an organism. The cells or tissues can be cultured cells or tissues. Alternatively, the cells or tissues are disposed within a living organism. In one embodiment, the medium includes a biomaterial. The biomaterial can be included in an extracorporeal shunt system for cells or tissues of a living organism.

Other features and advantages of the invention will be understood by reference to the drawings, detailed description and examples that follow.

BRIEF DESCRIPTION OF THE DRAWINGS

FIG. 2. Alignment of the amino acid sequence of human factor H (SEQ ID NO:1; see Ripoche J et al., 1988, *Biochem J* 249: 593-602) and an exemplary mini-FH (SEQ ID NO:2), showing the domains that were included and a poly-Gly linker.

FIG. 4. Binding activity and specificity of mini-FH, FH and terminal FH fragments 1-4 and 19-20. (A) Relative binding intensities for C3b, iC3b, C3dg are shown (three surfaces on one biosensor were coated physiologically with equal molar amounts of C3b prior to processing by Factor I). Responses were normalized to the highest signal within each set of analyte. (B) Fitted affinity curves for C3b are displayed when responses were normalized to $R_{max}$, Mini-FH and FH are leftmost curves, nearly superimposed; FH 19-20 is next right; FH 1-4 is far right.

FIG. 6. Protection of PNH erythrocytes. (A) Acidified serum was spiked with analytes prior to co-incubation with PNH-induced RBCs. In PBS-MgEGTA alone, about half of the erythrocytes lysed due to underregulation of the AP on the RBC-surface leading to MAC formation and sub-sequent lysis (determined by absorbance at 405 nm). In the presence of EDTA the AP activation was blocked and no lysis occurred. Abs$_{405}$ of RBCs resuspended in H$_2$O marks total hemoglobin release of a 100% of RBCs as a reference point. (B) Same assay as in (A), but half of the erythrocytes were subjected to desialylation with neuraminidase, prior to incubation with analyte spiked serum. Selected analyte concentrations which bracket the IC$_{50}$ value, as determined under (A), were chosen for this comparative assay. The inhibition curves of FH1-4 and the cyclic peptide CP30 perfectly overlay for ND-treated and untreated cells. Controls as above. (C) Lysis of patient derived PNH erythrocytes that were incubated in acidified serum spiked with analytes as above. For A and B: Analytes measured at a single concentration point were analyzed as triplicates, all others in duplicates. Standard deviation is shown. (A) is one representative assay of three independently performed assays and (B) is one representative assay from a total of two.

DETAILED DESCRIPTION OF ILLUSTRATIVE EMBODIMENTS

Figure 1:
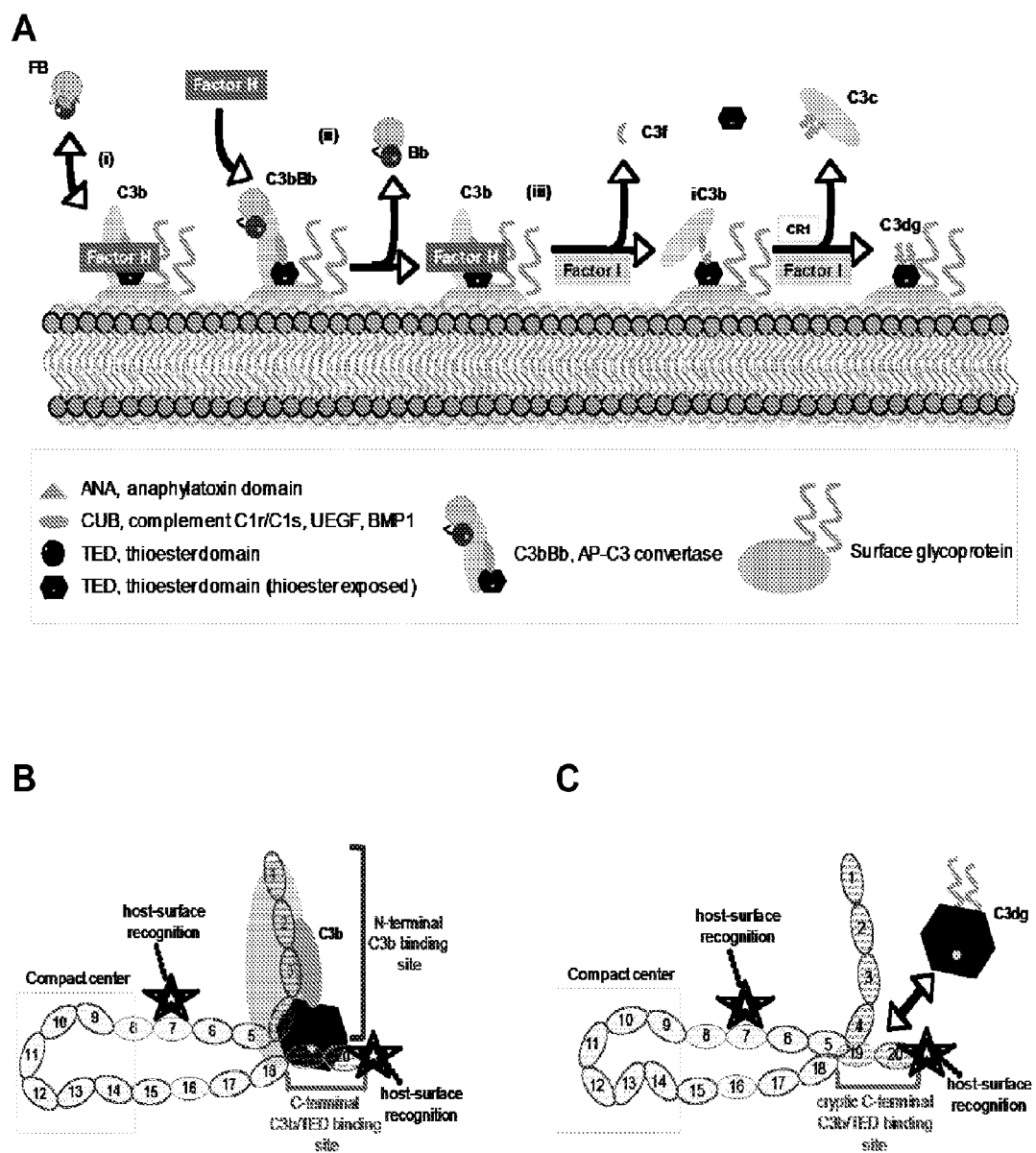
FIG. 1. Illustration of FH complement regulation and current model of binding to its chief interaction partner C3b on a host surface. (A) FH specifically regulates the AP-activation and amplification loop by (i) competing with Factor B for C3b-binding, (ii) accelerating the decay of AP C3-convertases and (iii) acting as a cofactor for enzymatic inactivation of C3b into iC3b by Factor I. In the presence of other complement receptor 1 (CR1), iC3b is further proteolyzed into C3dg and C3c. (B) FH has 20 complement control protein (CCP) domains. The N-terminal four domains (FH1-4) have been reported to bind C3b with an affinity of 10-13 µM and host the complement regulatory functions. The C-terminal CCPs 19-20 accommodate the major host recognition function and also harbor a second C3b binding site within the TED. Both termini in FH cooperate to bind to one C3b molecule at the same time, resulting in an affinity of about 1 µM. Simultaneous recognition of C3b and host-surface markers restricts efficient complement control to host structures. (C) illustrates the hypothesis of a compact conformation of FH that restrains the interaction of a cryptic C-terminus with C3b-inactivation products iC3b and C3dg.
Figure 3:
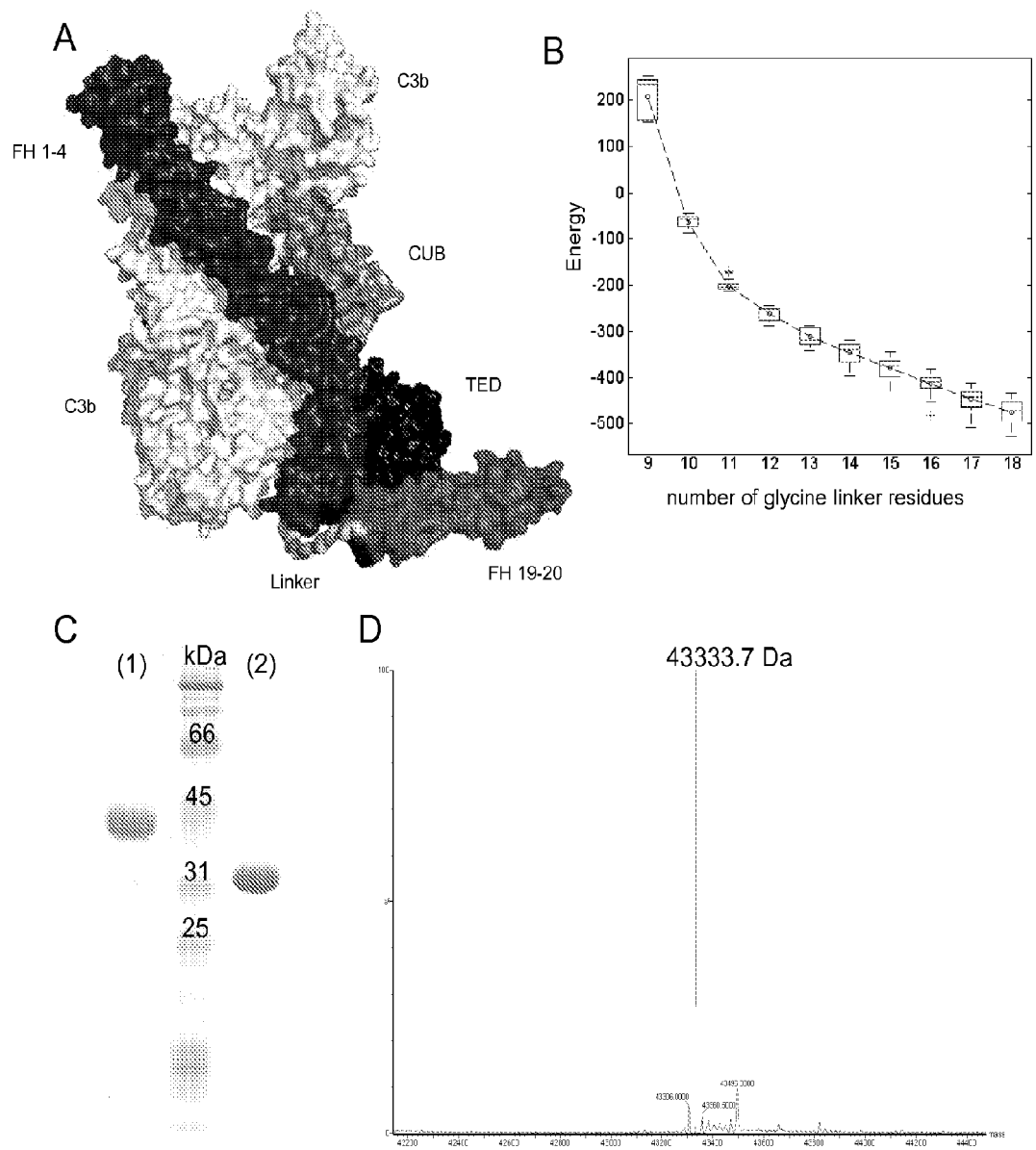
FIG. 3. Design and expression of mini-FH. (A) One alanine and 12 glycine residues connect the C-terminal residue E264 of CCP domains FH1-4 with the N-terminal residue G1107 of CCP domains FH19-20. All residues are shown as surface representation. C3b is light grey, apart from CUB-domain in dark grey and the TED in black. C3d, which correspondents to TED, is also shown in black. FH1-4 (blue in color figure) diagonally transverses C3b from upper left to lower right. FH19-20 (red in color figure) is just beneath TED and extends right. The 12 linking glycine residues (colored "by element" in color figure) connect FH 1-4 to FH 19-20. (B) Energy of modeled complexes versus number of glycine linker residues. The box plot shows the energy distribution of the top 80 models of each linker length. The circle and dashed line show the change of the average energy of these linkers. The energy drops quickly from 9 to 11, indicating that the linkers become relaxed during the extension. For linkers longer than 12 glycines, each additional glycine introduces similar energy difference. (C) Mini-FH was obtained recombinantly at high purity when analyzed on 12% SDS-PAGE with Coomassie blue staining Both, under reducing (lane 1) and non-reducing (lane 2) conditions, mini-FH emerges as an intense clean band at the expected size. Faster mobility under non-reduced indicates presence of disulfide bonds. (B) Deconvoluted ESI-mass spectrum of mini-FH shows one dominant peak, which is consistent with the theoretical mass of the mini-FH polypeptide chain and confirms identity and high degree of purity of the preparation.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, protein chemistry and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

A "complement regulator" as used herein is an agent that possesses the type of complement regulating activity found in the family of mammalian proteins known as the regulator of complement activation (RCA) family, also referred to herein as "RCA proteins", which regulate complement activity through the AP. RCA proteins impair the generation of new C3b by accelerating the decay of the C3 convertases or act as cofactor for factor 1 (F1) in degrading existing C3b. RCA proteins include cell surface-bound proteins such as decay accelerating factor (DAF), membrane cofactor protein (MCP) and complement receptor 1 (CR1), as well as the soluble factor H (FH), which controls the steady-state alternative pathway activation in circulation and on surfaces to which it specifically binds.

The terms "complement control protein (CCP) domain or module", "complement control protein (CCP), "short consensus repeat" (SCR) and "sushi domain" are used interchangeably herein to describe domains found in all RCAs that contribute to their ability to regulate complement activation in the blood or on host cell surfaces to which they specifically bind. CCPs typically are composed of about 60 amino acids, with four cysteine residues disulfide bonded in a 1-3 2-4 arrangement and a hydrophobic core built around an almost invariant tryptophan residue.

The terms "host" and "self" are used interchangeably herein to describe cells or tissues belonging to a particular organism, as compared to foreign cells, e.g., of invading microorganisms, or abnormal cells, which the immune system is designed to recognize as "other" or "non-self."

A "subject", "individual" or "patient" refers to an animal of any species. In various embodiments, the animal is a mammal. In one embodiment, the mammal is a human. In another embodiment, the mammal is a non-human animal.

"Treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient. "Treating" can also refer to reducing or eliminating a condition of a part of the body, such as a cell, tissue or bodily fluid, e.g., blood.

"Preventing" refers to the partial or complete prevention of the disease or condition in an individual or in a population, or in a part of the body, such as a cell, tissue or bodily fluid (e.g., blood). The term "prevention" does not establish a requirement for complete prevention of a disease or condition in the entirety of the treated population of individuals or cells, tissues or fluids of individuals.

The term "treat or prevent" is sometimes used herein to refer to a method that results in some level of treatment or amelioration of the disease or condition, and contemplates a range of results directed to that end, including but not restricted to prevention of the condition entirely.

A "prophylactic" treatment is a treatment administered to a subject (or sample) that does not exhibit signs of a disease or condition, or exhibits only early signs of the disease or condition, for the purpose of decreasing the risk of developing pathology associated with the disease or condition. This term may be used interchangeably with the term "preventing," again with the understanding that such prophylactic treatment or "prevention" does not establish a requirement for complete prevention of a disease in the entirety of the treated population of individuals or tissues, cells or bodily fluids.

As used herein, a "therapeutically effective amount" or simply an "effective amount" is the amount of a composition sufficient to provide a beneficial effect to the individual to whom the composition is administered, or who is otherwise treated using a method involving the composition.

The term "extracorporeal treatment" as used herein refers generally to treatment or manipulation of cells, tissues or bodily fluids that have been removed from an individual and are thereafter returned to the same individual or to another individual. Examples of extracorporeal treatments include, but are not limited to, extracorporeal shunting of blood during surgical procedures, for example, hemodialysis, and cell or tissue transplantation, to name a few.

The term "biomaterials" as used herein refers to components of equipment, devices or articles that come into contact with, biological substances such as cells, tissues or biological fluids, such as those being subjected to the extracorporeal treatment, or tissues surrounding an implanted device or tissue, such as stents, tubes, artificial tissues or other implants.

Dosages expressed herein are in units per kilogram of body weight (e.g., µg/kg or mg/kg) unless expressed otherwise.

Ranges are used herein in shorthand, to avoid having to list and describe each and every value within the range. Any appropriate value within the range is intended to be included in the present invention, as is the lower terminus and upper terminus, independent of each other.

The term "about" as used herein when referring to a measurable value such as an amount, a temporal duration, and the like, is meant to encompass variations of ±20% or ±10%, in some embodiments±5%, in some embodiments±1%, and in some embodiments±0.1% from the specified value, as such variations are appropriate to practice the disclosed methods or to make and used the disclosed compounds, compositions or articles of manufacture.

The articles "a" and "an" are used herein to refer to one or to more than one (i.e., to at least one) of the grammatical object of the article. By way of example, "an element" means one element or more than one element.

As used herein "comprising" is to be interpreted as specifying the presence of the stated features, integers, steps, or components as referred to, but does not preclude the presence or addition of one or more features, integers, steps, or components, or groups thereof. Thus, for example, a container comprising one tab may have two or three tabs. Additionally, the term "comprising" is intended to include embodiments encompassed by the terms "consisting essentially of" and "consisting of" Similarly, the term "consisting essentially of" is intended to include embodiments encompassed by the term "consisting of."

The present invention springs in part from the inventors' rational design and development of a recombinant protein therapeutic (mini-FH) by joining the four N-terminal and two C-terminal domains of FH, from a total number of 20, through an optimized linker in such a way that FH functionality is preserved. Importantly, the design attributes a novel function to mini-FH in that mini-FH shows a strong preference over FH in binding complement inactivation products. Thus mini-FH targets to and protects host cells via its simultaneous recognition of (i) complement activation/inactivation products and (ii) polyanionic host surface markers. When probed in an AP-mediated disease assay on patient-derived cells, mini-FH conferred efficient complement regulation at an $IC_{50}$ of approximately 0.02 μM.

To construct an exemplary targeted AP-specific regulator, the inventors analyzed available structure-function data on the major AP-regulator FH, reconciled apparently contradictory findings with a hypothesis on how FH works, tested this hypothesis experimentally and employed it for the rational design of the novel protein-therapeutic mini-FH.

The inventors surmised that a compact conformation of FH (Oppermann M et al., 2006, Clin Exp Immunol 144: 342-352; Schmidt C Q et al., 2010, J Mol Biol 395: 105-122; Aslam M & Perkins S J, 2001, J Mol Biol 309: 1117-1138) prevents unhindered engagement of FH C-terminal modules with TED on inactivated C3b (cf. FIG. 1C with FIG. 1B). Only simultaneous engagement of both FH termini, as seen for C3b, efficiently releases the cryptic conformation. As a consequence, the inventors predicted disproportionately high loss of FH binding-signals as one FH-binding site on C3b gradually disappears in the transition to iC3b and C3dg. The inventors employed this prediction to equip a FH-based inhibitor with a unique multiple-targeting mechanism for simultaneous recognition of C3b-inactivation products and host-surfaces, which maintains full FH functionality, but substantially surpasses the template molecule FH in controlling AP-activation on PNH erythrocytes.

Compositions:

One aspect of the present invention thus features a complement regulator that is uniquely targeted to the AP. The complement regulator comprises a complement regulating region that includes at least 3, preferably 4, complement control protein domains (CCPs), linked by a flexible linker to a multifunctional binding region that enables binding of the complement regulator to one or more C3b activation/inactivation products and/or one or more oxidation end products, as well as to polyanionic surface markers on host cells.

Because CCPs are found in all RCAs, they can be derived from any RCA. Suitable RCAs from which CCPs may be derived include, but are not limited to Factor H, decay accelerating factor (DAF, CD55), complement receptor 1 (CR1, CD35), membrane cofactor protein (MCP, CD46), C4 binding protein (C4BP) or Smallpox inhibitor of complement enzymes (SPICE). In one embodiment, the CCPs are derived from FH. Any FH can serve as the source of those CCPs. One embodiment utilizes human FH as the source of CCPs. In one embodiment, the CCPs are derived from SCRs 1-4 of FH, such as human FH.

The multifunctional binding region of the complement regulator binds to one or more C3 activation/inactivation products, to polyanionic surface markers on host cells and optionally advanced oxidation end products. Such C3 activation/inactivation products include but are not limited to thioester domain (TED)-containing C3 fragments, namely C3b, iC3b, C3dg and C3d. The polyanionic surface markers on host cells include but are not limited to N-linked glycosylation with sialic acid end-groups and diverse glycosaminoglycans (GAGs) like heparin, heparan sulfate, chondroitin sulfate, dermantan sulfate, keratan sulfate and hyaluronan. The oxidation end products include but are not limited to malondialdehyde (MDA), 4-hydroxynonenal (4-HNE), carboxyethylpyrrole (CEP), oxidized phosphatidylserine (OxPS), oxidized cardiolipin (OxCL) and phosphocholine (PC).

In one embodiment, the multifunctional binding region is derived from SCRs (CCPs) 19 and/or 20 of FH; preferably both SCRs 19 and 20 are utilized. In other embodiments, SCRs 6-8 of FH, and/or SCR 13 of FH, can be utilized as an alternative or supplement to SCRs 19 and/or 20. Additionally, domains in other proteins that bind glycosaminoglycans (GAGs) may also be suitable for polyanion targeting, particularly in combination with other domains. Examples of such proteins include hepatocyte growth factor, which acts upon endothelial cells in a manner similar to FH, and antithrombin, which also binds heparin.

The complement regulatory region is linked to the multifunctional binding region by a flexible linker designed to provide appropriate spacing between the two regions to enable each region to function for its intended purpose, either on its own or cooperatively. The linker may be peptidic, non-peptidic or partially peptidic. In certain embodiments, the linker is of substantially the same length and flexibility as a poly-Gly peptide at least 9 residues in length, or at least 10 residues in length, or at least 11 residues in length, or at least 12 residues in length, or at least 13 residues in length, or at least 14 residues in length, or at least 15 residues in length, or at least 16 residues in length, or at least 17 residues in length, or at least 18 residues in length. In certain embodiments, the linker is of substantially the same length and flexibility as a poly-Gly peptide up to 18 residues in length. An exemplary embodiment utilizes a poly-Gly peptide at least 12 residues in length. Other amino acid residues, or analogs of such residues, may be included in the linker. For instance, addition of one or more Ala residues into the linker may introduce beneficial features while also maintaining the relative size and flexibility of the linker Substitution of a single Gly residue in the exemplary linker with another residue is not likely to substantially alter the features of the linker. If additional substitutions are made, in may be beneficial to increase the overall linker length to maintain proper flexibility (e.g., a 17 residue linker with 15 Gly residues and two other residues).

The two regions can be linked together in either order; i.e., the complement regulatory region can be on the amino-terminal side of the linker and the multifunctional binding region can be on the carboxy-terminal side of the linker, or the arrangement can be reversed such that the multifunctional binding region is on the N-terminal side of the linker and the complement regulatory region is on the C-terminal side of the linker. In one embodiment, the complement regulator comprises, from N- to C-terminus, SCRs 1-4 of FH, a poly-Gly linker at least 9, or 10, or 11, or 12, or 13, or 14, or 15, or 16, or 17, or 18 residues in length, and SCRs 19-20 of FH. In a particular embodiment, the functional elements are derived from human FH, including but not limited to the human FH represented by SEQ ID NO:1 herein. FH domains 19-20 may exhibit surface recognition functions in species other than human, particularly in higher mammals. There is significant sequence conservation for Factor H across the species, especially for the regulatory domains 1-4 and the recognition domain 19-20 (see, e.g., Schmidt C Q et al., 2010, supra (supplement). Thus, examples of suitable FH molecules include but are not limited to those found under GenBank Accession Nos. AAI42700 (human), ABB02180 (human), CAA68704 (human), CAI19672 (human), NP_000177 (human), PO8603 (human), NP_034018 (mouse), PO6909 (mouse), CAC67513 (rat), NP_569093 (rat), AAI05259 (cow), NP_001029108 (cow), CAC81999 (pig) and NP_999446 (pig), to name a few.

In an exemplary embodiment, the complement regulator is a polypeptide referred to herein as "mini-FH," and comprises the amino acid sequence represented by SEQ ID NO:2 or a functional equivalent. By "functional equivalent," it is meant that the precise sequence can vary, but only to the extent that each functional element still performs the recited function, e.g., complement regulation, multifunctional binding and flexible linking. In certain embodiments, functional equivalents comprise an amino acid sequence at least 80% identical to that of SEQ ID NO:2, excluding the linker. In other embodiments, functional equivalents comprise an amino acid sequence at least 81%, or 82%, or 83%, or 84%, or 85%, or 86%, or 87%, or 88%, or 89%, or 90%, or 91%, or 92%, or 93%, or 94%, or 95%, or 96%, or 97%, or 98%, or 99% identical to that of SEQ ID NO:2, excluding the linker.

The exemplary complement regulator, mini-FH, displays several improved properties as compared with FH and with other agents known to regulate AP-mediated complement activation. For instance, the experimental results set forth in Example 1 demonstrate that mini-FH shows a strong preference over FH in binding complement inactivation products. Thus, mini-FH targets to and protects host cells via its simultaneous recognition of complement activation/inactivation products and polyanionic host surface markers. When probed in an AP-mediated disease assay on PNH patient-derived erythrocytes, mini-FH conferred efficient complement regulation at an $IC_{50}$ of approximately 0.02 µM. In that assay, 0.06 to 0.1 µM of mini-FH stopped AP-mediated lysis completely. By comparison, addition of FH to a concentration of 1 µM was needed to stop lysis completely.

Using a similar assay, Ristano et al. (2010, ASH Annual Meeting Abstracts, *Blood* 116: Abstract 637), reported an $IC_{50}$ of the chimeric peptide TT30 of 30 µg/ml, or 0.48 µM based on an estimated molecular weight of 63 kDa which corresponds to the 9 CCPs comprising TT30. Thus, mini-FH was over ten-fold more active than TT30 in an in vitro protection assay of patient-derived PNH erythrocytes.

The complement regulators of the present invention can be prepared by various synthetic methods of peptide synthesis via condensation of one or more amino acid residues, in accordance with conventional peptide synthesis methods. For example, peptides are synthesized according to standard solid-phase methodologies, such as may be performed on an Applied Biosystems Model 431A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly-known protecting groups.

Alternatively, certain types of complement regulators can be produced by expression in a suitable prokaryotic or eukaryotic system. For example, a DNA construct can be inserted into a plasmid vector adapted for expression in a bacterial cell (such as *E. coli*) or a yeast cell (such as *Saccharomyces cerevisiae* or *Pichia pastoris*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences. In an exemplary embodiment, a FH-based complement regulator is produced by expression in *Pichia pastoris*, and thereafter purified in accordance with known methods, as summarized in Example 1.

Polypeptides produced by gene expression in a recombinant procaryotic or eucaryotic system can be purified according to methods known in the art. A combination of gene expression and synthetic methods may also be utilized to produce the complement regulators. For example, a polypeptide can be produced by gene expression and thereafter subjected to one or more post-translational synthetic processes.

Another aspect of the invention features a pharmaceutical composition comprising the complement regulator described above and a pharmaceutically acceptable carrier. Such a pharmaceutical composition may include the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-does unit.

As used herein, the term "pharmaceutically-acceptable carrier" means a chemical composition with which a complement regulator may be combined and which, following the combination, can be used to administer the complement regulator to an individual.

As used herein, the term "physiologically acceptable" ester or salt means an ester or salt form of the active ingredient which is compatible with any other ingredients of the pharmaceutical composition, which is not deleterious to the subject to which the composition is to be administered.

The pharmaceutical compositions useful for practicing the invention may be administered to deliver a dose of between 1 ng/kg and 100 mg/kg body weight as a single bolus, or in a repeated regimen, or a combination thereof as readily determined by the skilled artisan. In certain embodiments, the dosage comprises at least 0.1 mg/kg, or at least 0.2 mg/kg, or at least 0.3 mg/kg, or at least 0.4 mg/kg, or at least 0.5 mg/kg, or at least 0.6 mg/kg, or at least 0.7 mg/kg, or at least 0.8 mg/kg, or at least 0.9 mg/kg, or at least 1 mg/kg, or at least 2 mg/kg, or at least 3 mg/kg, or at least 4 mg/kg, or at least 5 mg/kg, or at least 6 mg/kg, or at least 7 mg/kg, or at least 8 mg/kg, or at least 9 mg/kg, or at least 10 mg/kg, or at least 15 mg/kg, or at least 20 mg/kg, or at least 25 mg/kg, or at least 30 mg/kg, or at least 35 mg/kg, or at least 40 mg/kg, or at least 45 mg/kg, or at least 50 mg/kg, or at least 55 mg/kg, or at least 60 mg/kg, or at least 65 mg/kg, or at least 70 m/kg, or at least 75 mg/kg, or at least 80 mg/kg, or at least 85 mg/kg, or at least 90 mg/kg, or at least 95 mg/kg, or at least 100 mg/kg, on a daily basis or on another suitable periodic regimen. In a particular embodiment, the dosage is between about 0.5 mg/kg and about 20 mg/kg, or between about 1 mg/kg and about 10 mg/kg, or between about 2 mg/kg and about 6 mg/kg, based on preclinical studies of TT30 (Fridkis-Hareli et al., 2011, supra) and taking into account the comparatively greater efficacy of mini-FH in an in vitro assay.

In one embodiment, the invention envisions administration of a dose that results in a serum concentration of the complement regulator between about 0.01 µM and 10 µM in an individual. In certain embodiments, the combined dose and regimen will result in a serum concentration, or an average serum concentration over time, of the complement regulator of at least about 0.01 µM, or at least about 0.02 µM, or at least about 0.03 µM, or at least about 0.04 µM, or at least about 0.05 µM, or at least about 0.06 µMl, or at least about 0.07 µM, or at least about 0.08 µM, or at least about 0.09 µM, or at least about 0.1 µM, 0.11 µM, or at least about 0.12 µM, or at least about 0.13 µM, or at least about 0.14 µM, or at least about 0.15 µM, or at least about 0.16 µM, or at least about 0.17 µM, or at least about 0.18 µM, or at least about 0.19 µM, or at least about 0.2 µM, or at least about 0.3 µM, or at least about 0.4 µM, or at least about 0.5 µM, or at least about 0.6 µM, or at least about 0.7 µM, or at least about 0.8 µM, or at least about 0.9 µM, or at least about 1 µM or at least about 1.5 µM, or at least about 2 µM, or at least about 2.5 µM, or at least about 3 µM, or at least about 3.5 µM, or at least about 4 µM, or at least about 4.5 µM, or at least about 5 µM, or at least about 5.5 µM, or at least about 6 µM, or at least about 6.5 µM, or at least about 7 µM, or at least about 7.5 µM, or at least about 8 µM, or at least about 8.5 µM, or at least about 9 µM, or at least about 9.5 µM, or at least about 10 µM. In certain embodiments, the combined dose and regimen will result in a serum concentration, or an average serum concentration over time, of the complement regulator of up to about 0.1 µM, 0.11 µM, or up to about 0.12 µM, or up to about 0.13 µM, or up to about 0.14 µM, or up to about 0.15 µM, or up to about 0.16 µM, or up to about 0.17 µM, or up to about 0.18 µM, or up to about 0.19 µM, or up to about 0.2 µM, or up to about 0.3 µM, or up to about 0.4 µM, or up to about 0.5 µM, or up to about 0.6 µM, or up to about 0.7 µM, or up to about 0.8 µM, or up to about 0.9 µM, or up to about 1 µM or up to about 1.5 µM, or up to about 2 µM, or up to about 2.5 µM, or up to about 3 µM, or up to about 3.5 µM, or up to about 4 µM, or up to about 4.5 µM, or up to about 5 µM, or up to about 5.5 µM, or up to about 6 µM, or up to about 6.5 µM, or up to about 7 µM, or up to about 7.5 µM, or up to about 8 µM, or up to about 8.5 µM, or up to about 9 µM, or up to about 9.5 µM, or up to about 10 µM. While the precise dosage administered will vary depending upon any number of factors, including but not limited to, the type of patient and type of disease state being treated, the age of the patient and the route of administration, such dosage is readily determinable by the person of skill in the art.

The pharmaceutical composition can be administered to a patient as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the patient, as described above.

Pharmaceutical compositions that are useful in the methods of the invention may be administered systemically in oral solid formulations, parenteral, ophthalmic (including intravitreal), suppository, aerosol, topical or other similar formulations. Such pharmaceutical compositions may contain pharmaceutically acceptable carriers and other ingredients known to enhance and facilitate drug administration. Other formulations, such as nanoparticles, liposomes, resealed erythrocytes, and immunologically based systems may also be used to administer a complement inhibitor according to the methods of the invention.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution can be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, in microbubbles for ultrasound-released delivery or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents including replacement pulmonary surfactants; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics;

antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa.

Methods:

Another aspect of the invention features methods of regulating complement activation. In particular embodiments, practice of the methods results in modulation of complement activation via the AP. In general, the methods comprise contacting a medium in which regulation of complement activation is desired with a complement regulator of the present invention, wherein the contacting results in regulation of complement activation in the medium. The medium can be any medium in which regulation of complement activation is desired. In certain embodiments, the medium includes cells or tissues of an organism, including (1) cultured cells or tissues, (2) cells or tissues within the body of a subject or patient, and (3) cells or tissues that have been removed from the body of one subject and will be replaced into the body of the same patient (e.g., extracorporeal shunting of blood or autologous transplantation) or transferred to another patient. In connection with the latter embodiment, the medium may further comprise a biomaterial, such as tubing, filters or membranes, that contact the cells or tissues during extracorporeal shunting. Alternatively, the medium may comprise biomaterials that are implanted into a subject.

In certain embodiments, the methods of regulating complement activation apply to living patients or subjects and comprise part or all of a method of treating the patient for a pathological condition associated with complement activation, particularly AP-mediated complement activation. Many such pathological conditions are known in the art (see, e.g., Holers, 2008, supra) and include, but are not limited to, as atypical hemolytic uremic syndrome (aHUS), dense deposit disease, age-related macular degeneration (AMD), paroxysomal nocturnal hemoglobinuria (PNH), rheumatoid arthritis (RA), systemic lupus erythematosus (SLE), several autoimmune and autoinflammatory kidney diseases, autoimmune myocarditis, multiple sclerosis, traumatic brain and spinal cord injury, intestinal and renal ischemia-reperfusion (IR) injury, spontaneous and recurrent pregnancy loss, anti-phospholipid syndrome (APS), asthma, anti-nuclear cytoplasmic antigen-associated pauci-immune vasculitis (Wegener's syndrome), non-lupus autoimmune skin diseases such as pemphigus, bullous pemphigoid, and epidermolysis bullosa, post-traumatic shock and atherosclerosis. In particular embodiments, the pathological condition has been associated with mutations and polymorphisms in the gene encoding FH, including but not limited to: AMD, aHUS and membrano-proliferative glomerulonephritis type II (MPGN-II, also referred to as dense deposit disease (DDD)). In other embodiments, the complement regulators of the present invention are suitable for use as a substitute for Eculizumab or TT30 in treatment of diseases for which those agents are currently prescribed, or for which they are being developed in pre-clinical and clinical studies. Those diseases include, but are not limited to, aHUS, PNH and AMD.

The treatment methods typically comprise (1) identifying a subject with a disease or condition treatable by regulation of complement activation as described hereinabove, and (2) administering to the subject an effective amount of a complement regulator of the invention using a treatment regimen and duration appropriate for the condition being treated. Development of appropriate dosages and treatment regimens will vary depending upon any number of factors, including but not limited to, the type of patient and type of disease state being treated, the age of the patient and the route of administration. The skilled artisan is familiar with the design of dosage regimens that take such variables into account. As one example, a dosage regimen similar to that of Eculizumab may be developed for treatment of PNH or aHUS with a complement regulator of the invention, taking into account the difference in potency between the two substances. Eculizumab typically is administered by intravenous infusion for treatment of PNH or aHUS according to the following schedule: 600 mg weekly for the first 4 weeks, 900 mg for the fifth dose 1 week later, then 900 mg every 2 weeks thereafter (Alexion Pharmaceuticals, Inc. Package Insert version dated "Last Revised 28 Sep. 2011"). As another example, a dosage regimen based on preclinical and clinical results developed for similar agents may be utilized. For example, a pharmacokinetic study of the chimeric protein TT30 in cynomolgus monkeys revealed that an intravenous or subcutaneous bolus of 15-60 mg/kg resulted in inhibition of complement AP activity for several to many hours (Fridkis-Hareli et al., 2011, supra). The skilled artisan can readily develop a dosage and regimen for the complement regulators of the invention based on this type of information.

The following example is provided to describe the invention in greater detail. It is intended to illustrate, not to limit, the invention.

Example 1

This example describes the synthesis of mini-FH and demonstration of its ability to regulate complement activation through the AP.

Materials and Methods

Surface plasmon Resonance.

All sensorgrams were recorded on a Biacore 2000 instrument (GE Healthcare Corp., Piscataway, N.J.), processed in Scrubber (v2.0c; BioLogic Pty, Australia), and are shown as duplicates of dummy surface-subtracted response curves.

C3-Fragment Binding.

Equal amounts of C3b (~4000 RUs) (from Complement Technology, Tyler, Tex., USA) were immobilized onto 3 flow-cells (fc) of a CM5 chip (Biacore) by initial amine-coupling of a small amount of C3b onto fc 2-4 and further deposition of the vast majority of C3b molecules via its reactive thioester through an on-chip assembly of the AP-convertase (C3bBb) and subsequent exposure to and proteolytic activation of C3 (24). The surface was washed overnight with a buffer flow of 10 ul/min to allow stabilization of the physiologically prepared C3b-surface. Test-injections of 1 µM FH or 10 µFH19-20 yielded similar response units (RUs) for all three C3b surfaces (on fc 2-4: 600, 680 and 690 RUs for FH and 240, 230 and 230 RUs for FH19-20, respectively) and proved very similar loadings of C3b molecules. C3b molecules on fc3 and fc4 were processed with FI in the presence of the cofactors FH or soluble complement receptor 1 (sCR1) to yield iC3b or C3dg (the latter as described in Morgan et al., 2011, supra), respectively. A dummy surface (fc1) was prepared by two consecutive cycles of surface activation with standard amine coupling reagents and quenching by ethanolamine.

Successful processing to iC3b and C3dg was demonstrated with injections of sCR1 and FH15-18. As expected, FH15-18 did not associate with either of the deposited C3-opsonins (Morgan et al., 2011, supra), while sCR1 at 0.33 μM showed a strong binding to the C3b surface (925 RUs), a moderate to weak response to the iC3b surface (245 RUs) and negligible binding to the C3dg surface (15 RUs) consistent with previous findings. Due to the physiological deposition of C3b and subsequent trimming with FI, both, the iC3b and the C3dg, surfaces likely carry miniscule amounts of residual C3b molecules, which were not readily accessible by FI. However, the predicted responses of the positive and negative control, sCR1 and FH15-18, show that the physiological processing worked close to completion. Deposition, proteolytic processing and all interactions studies were performed in HBS-P+buffer (i.e. 10 mM HEPES-buffered 150 mM saline (pH7.4), 0.005% (v/v) surfactant p20, 1 mM $MgCl_2$) at 25° C.

Decay Acceleration Assay.

Similarly as described above C3b was immobilized onto a CM5-chip by initially fixing some C3b via amine coupling (2740RUs) and subsequent physiological deposition of the majority of C3b molecules (5090RUs) through the reactive thioester of C3b in the presence of the AP-convertase. An extensive wash with buffer was performed as above. A mix of 100 nM Factor D and 500 nM Factor B in running buffer (10 mM HEPES, 150 mM NaCl, 0.005% (vol/vol) Tween-20 and 1 mM $MgCl_2$, pH 7.4) was flowed for 3 min at 10 μl/min over the immobilized C3b-surface to build the AP-convertase C3bBb on the chip. Following an undisturbed decay of 1 min, the analytes, all at 100 nM, were injected for 3.5 min. To regenerate the surface, residual convertases were decayed by consecutive injections of 2 μM FH1-4 and 1 M NaCl. For comparative visualization of the decay acceleration response, SPR signals of the analytes obtained for C3b in the absence of the convertase were subtracted from the respective once obtained in presence of the convertase. Scaling up to a maximum of 5% was performed on some response curves to compensate for the small drift in signal due to the physiological immobilization procedure in order to facilitate an excellent overlay of sensorgrams at the time point of analyte injection.

Computational Modeling.

The complex structure of C3b:mini-factor H was constructed by superposing the C3d domain (or TED) of the C3b:FH1-4 (2WII, Wu et al., 2009, supra) and C3d:FH19-20 (3OXU, Morgan et al., 2011, supra) complex structures. The root mean square distance between two superposed C3d domains was 0.285 Å. The linker between CCP4 and CCP19 was modeled by the dope_loopmodel module of MODELLER 9v8 (25). The energy of dope_loopmodel, which is the energy we used to evaluate the model of mini-FH, with different linker length, bound to C3b, is composed by several terms, including bond length, bond angle, torsion, improper torsion, dihedral, 6-12 Lennard-Jones potential, DOPE potential and GBSA solvent potential. For each linker length, 100 conformations were sampled. The top 80 models of each linker length were selected to evaluate the effect of different length on energy and conformation.

Heparin Chromatography.

A 5 ml HiTrap heparin column equilibrated in PBS was used. Elution was performed by applying a linear gradient from PBS to PBS substituted with 0.5 M NaCl in 5 column volumes.

Cofactor Activity.

A fluid phase, time-course cofactor assay was performed in PBS, similar to Schmidt et al., 2011, supra. A mastermix of Factor I, C3b (both from Complement Technology) and respective cofactor (added last) was kept on ice and aliquoted into 20 μl aliquots prior to incubation at 37° C. for increasing amounts of time (as specified in FIG. 5A). A mix in absence of any cofactor served as negative control. In the final reaction, C3b was at a concentration of 0.7 μM, Factor I at 0.01 μM, and FH or mini-FH at 0.1 μM.

Classical Pathway ELISA.

Nunc maxisorb 96-well plates were coated with 1% ovalbumin (Sigma) in PBS, pH 7.4, 50μ/well for 2 h at room temperature (RT) or overnight (O/N) at 4° C. Washing twice with PBST (0.05% Tween 20), 200 μl/well was followed by blocking with 1% BSA (bovine serum albumin) in PBS, pH 7.4, 200 μl/well, for 1 h at RT. Then rabbit anti-ovalbumin antibody at a dilution of 1:1000 in 1% BSA/PBS, was bound for 1 h at RT (50 μl/well). After another washing step, as above, serial dilutions of analytes in PBS were added to the 96 well plate. To 10 μl of analyte, 20 μl of PBS++ (=PBS containing 1 mM $MgCl_2$ and 0.9 mM $CaCl_2$) was added into each well of the ELISA plate, followed by 30 μl of a 1:40 serum dilution in PBS++. The mix was incubated at RT for 15 min prior to another washing step as above and the subsequent exposure to goat anti-human C3 (HRP-conjugate from MP Biomedicals, LLC) at a 1:1000 dilution in 1% BSA/PBS, 50 μl/well for 30 min at RT. After washing three times with PBST, detection was achieved by adding 50 μl/well of a freshly mixed solution containing 0.1 M sodium citrate at pH 4.3, 5 mg ABTS (Roche) and 0.03% $H_2O_2$. Absorbance was measured at 405 nm. EDTA at a final concentration of 10 mM was used as negative control.

Alternative Pathway ELISA.

Nunc maxisorb 96 well plates were coated with 40 μg/ml LPS (lipopolysaccharide from Sigma), in PBS, pH 7.4, 50 μl/well for 2 h at room temperature (RT) or overnight (O/N) at 4° C. Washing, blocking, addition of analytes was performed as above. To 30 μl of analyte in PBS, 30 μl of a solution containing 50% serum and 10 mM MgEGTA in PBS was added. The mix was incubated for 1 h at 37° C. Negative control, washing and detection were performed as mentioned above.

Induction of PNH-Phenotype in Normal Erythrocytes and Protection/Lysis Assay.

Erythrocytes from a healthy donor were washed and treated (Ezzell J L et al., 1991, *Blood* 77: 2764-2773) in order to induce PNH phenotype (sensitized erythrocytes). A protection assay of those erythrocytes was performed similarly, but with a few modifications, as published (Ezzell et al., 1991, supra). In brief, erythrocytes were treated with an 8% solution of the sulfhydryl reagent 2-aminoethylisothiouronium-bromide (AET) and then washed with PBSE (=PBS containing 5 mM EDTA) and PBS. The concentration of red blood cells (RBC) in PBS was adjusted so that the absorbance at 405 nm of 100 μl of a dilution of 10 μl erythrocyte stock in 190 μl water yielded a value between 1.5 and 2.0. To such a stock an anti-DAF antibody (Clone: BRIC216, Isotype: IgG1, from SeroTech) was added to a final concentration of 6.7 μg/ml and the mix was incubated for 30 min on ice. After washing with PBS, the treated erythrocytes were resuspended with PBS-Mg (PBS containing 1 mM $MgCl_2$ at pH 6.4) to the initial volume (to yield the same concentration of RBCs) and subjected to the protection/lysis assay. When desialylated erythrocytes were used, a RBC suspension in PBS-Mg was split in half. Both halves were incubated at 37° C. on a rotating disk, but only one had been substituted with 36U of Neuraminidase (New England Biolabs) per 100 μl of RBC-stock.

Fresh human serum was acidified with 0.2 M HCl to pH 6.4 and substituted with $MgCl_2$ and EGTA to yield final concentrations of 2.5 mM and 8 mM, respectively. In a round bottom 96 well plate, 60 μl of this serum-mix were added to 10 μl PBS at pH 6.4 containing 1 mM MgCl$_2$ and 20 μl of analyte in PBS. The plate was shaken and incubated on ice for 5 min prior to pipetting 10 μl of sensitized, or sensitized and desialylated, RBC into each well. The final serum concentration in this reaction mix was 52%. The 96-well plate was incubate on a shaking platform for 30 min at 37° C. and thereafter the reaction was immediately quenched by addition of 100 μl ice-cold PBS containing 5 mM EDTA. Remaining, i.e. non-lysed, cells were separated by centrifugation at 1000 g for 3 min and 100 μl of the supernatant was transferred into a fresh 96-well plate to measure the absorbance at 405 nm.

Results:

Design Objectives.

To gain AP-specific regulatory function without blocking CP and LP, the new regulator was designed based on functional domains of FH, but was determined to be more potent than FH. The complement regulatory functions residing in FH CCPs 1-4 and the polyanion host surface recognition feature, which maps to FH CCPs 19-20, were included. With the incorporation of C-terminal CCPs 19-20, the recently described FH-function of localizing to and protection of sites of oxidative damage was also incorporated (Weismann D et al., 2011, *Nature* 478: 76-81). To gain extra potency in complement regulation over FH, the CCPs 1-4 and 19-20 were connected with a sufficient degree of flexibility so that the ability of FH19-20 to bind indiscriminately to all C3-opsonins would be unrestricted to allow efficient targeting to sites of complement inactivation, as opposed to a compact FH molecule which shows substantially reduced ability to bind iC3b. Finally, despite the flexibility needed for targeting of C3b-inactivation products, direct linking of CCPs 1-4 and 19-20 additionally requires that the new regulator matches the affinity of FH for its major target C3b. Accordingly, the new regulator was designed to occupy both FH-binding sites on C3b simultaneously to cooperate upon C3b-engagment.

Twelve Glycines Link the Four N- and Two C-Terminal Domains of FH without Imposing Restraints on C3b-Binding.

To design an unstructured linker with low immunogenic potential and high solubility any hydrophobic, bulky and charged amino acids were avoided (Schellenberger V, et al., 2009, *Nat Biotechnol* 27: 1186-1190) and glycine was chosen to insure a high degree of flexibility. Superimposition of the crystal structure complexes FH1-4:C3b and FH19-20:C3d (FIG. 3A) yielded a distance (from $C_\alpha$ to $C_\alpha$) of 35.3 Å between the C-terminal alanine (the C-terminal alanine follows directly after E264, which is the last native FH residue of the FH1-4 construct of Wu et al. (2009, supra) of the FH1-4 construct and the N-terminal glycine of CCP 19 (FH residue G1107, noting that all numbering of residues includes the signal peptide present). Given the maximum distance of 3.8 Å between two $C_\alpha$-atoms of two consecutive residues, a minimum of nine glycines were determined to be needed to span this distance.

Computational modeling was employed to optimize the number of linking glycine residues to provide enough space and flexibility as to allow the covalently linked CCPs 1-4 and 19-20 to bind simultaneously to C3b. In silico constructions of such fusion proteins were submitted to energy calculations. Two stages of energy change in relation to the number of linking glycines were found (FIG. 3B). In the first stage, a fast drop of energy was observed when the linker length increased from 9 to 11 due to the relaxation of local strain. In the second stage, as linker length increased from 12 to 18 residues, the decrease of energy became moderate. This slower drop of energy was caused by interactions introduced by the elongated linker Analysis of the sampled conformations of all linkers confirmed that linkers with 9-11 glycines were constrained while linkers of 12-18 glycines were relaxed. Thus, at least 12 glycines were found sufficient to connect the two functional termini of FH without imposing constraint upon simultaneous C3b binding. Those constructs were examined further.

Engineered Protein Mini-FH Obtained Recombinantly at High Purity.

Mini-FH was expressed in *Pichia pastoris* and purified using conservative chromatography methods, as detailed by Schmidt et al. (Schmidt C Q et al., 2011, *Protein Expr Purif* 76: 254-263). Briefly, codon-optimized coding DNA was cloned it into the Pst1-Xba1 restriction sites of vector pPICZalphaB (Invitrogen) and transformed into *P. pastoris*. The culture was expanded in a Bioflow 310 fermenter (New Brunswick Scientific) without deglycosylation and purified from the organism using SP-sepharose size exclusion and ion exchange chromatography.

Denaturing gel analysis of the purified protein under both reducing and non-reducing conditions showed a clean preparation in the absence of significant cleavage bands. The migration pattern was consistent with a 43.3 kDa protein that contained multiple (12 in total) disulfide bridges (FIG. 3C). ESI-mass spectrometry returned a mass of 43332.5 Da, which is in close agreement with the theoretical mass of 43333.7 Da. The outstanding peak in the deconvoluted mass spectrum (FIG. 3D) substantiates the high level of purity.

Binding Activities of Mini-FH and FH are Nearly Identical for C3b and Heparin, but Differ for the C3b-Inactivation Products iC3b and C3dg.

The analytes FH1-4, FH19-20, mini-FH and FH were tested for their ability to adhere to heparin, a model substance for polyanionic host surface markers, under physiological conditions in phosphate-buffered saline (PBS). FH1-4 did not bind to the model substance while FH and FH19-20 did bind to it. Mini-FH eluted slightly later than FH and just prior to FH19-20 from the heparin affinity column, which is consistent with the notion of all three proteins being able to recognize polyanionic host surfaces.

Surface plasmon resonance (SPR) was used to analyze the binding behavior between FH and mini-FH and the key functional FH sites, i.e. FH1-4 and FH19-20, with physiologically deposited C3-opsonins C3b, iC3b and C3dg (all at equal molar loading density) in physiological buffer. Binding of FH1-4 (FIG. 4A) to iC3b and C3dg was almost completely abolished when compared to C3b. While FH19-20 showed similar response levels for all three C3 opsonins, FH showed a prominent 57% and 81% reduced binding capacity for iC3b and C3dg in relation to C3b, respectively. In contrast to this, mini-FH preserved binding capacities for the C3b-inactivation products more similar to FH19-20. We then determined the binding affinities for C3b, the chief interaction partner of FH. FH1-4, FH19-20 and FH bound to deposited C3b (FIG. 4B) with the same affinities on amine coupled C3b as reported previously (Wu et al., 2009, supra). Mini-FH matched the affinity of FH for C3b. Complement functional tests were performed to test if the mini-FH feature of the markedly stronger binding capacity for iC3b and C3dg translated into an enhanced regulatory activity.

Mini-FH Retains Known FH Functionality but is Substantially More Active in Controlling AP-Activation.

When tested for their ability to accelerate the decay of AP-convertases C3bBb, assembled on a Biacore CM5 chip, FH19-20 failed to exhibit such activity, as reported before (Wu et al., 2009, supra). All other proteins assayed showed decay accelerating activity (DAA, FIG. 5B) to slightly various degrees. While FH1-4 and FH were almost identically active, mini-FH showed a more pronounced DAA.

Figure 5:
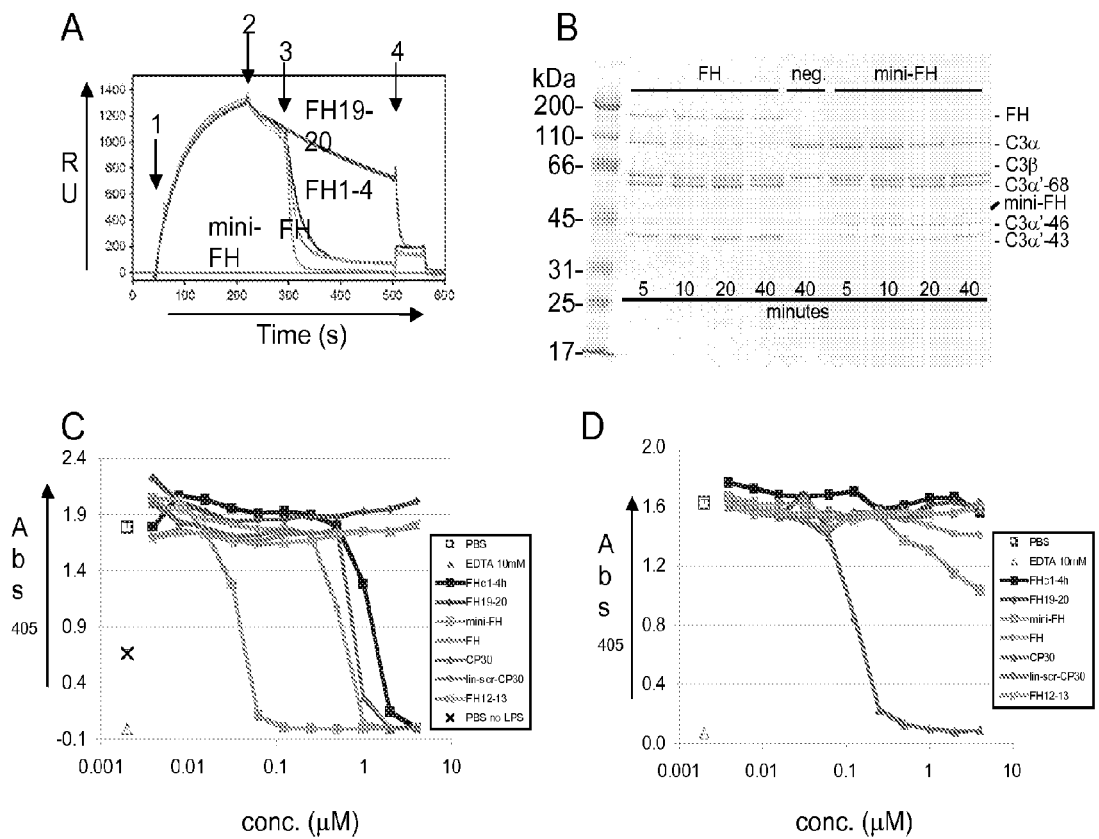
FIG. 5. Functional characterization of mini-FH, FH and terminal FH fragments 1-4 and 19-20. (A) DAA was analyzed by surface plasmon resonance (SPR). (#1) A mix of Factor B and Factor D were injected onto physiologically immobilized C3b to form AP-convertase C3bBb. (#2) For a short time C3bBb was allowed to undergo its slow, natural decay before (#3) injecting one of the analytes (each at 100 nM) at a time. At 500 s (#4) a 2 µM solution of FH1-4 was injected to decay any convertase that remained during analyte exposure. Only FH19-20 does not accelerate the decay of the convertase, which consequently dissociates slowly by its intrinsic decay rate. FH1-4, FH and mini-FH all have DAA. (B) Time course cofactor activity shows that both, FH and mini-FH, have cofactor activity. While at 40 min in presence of 0.1 µM FH, C3b is almost completely processed to iC3b$_2$ (as judged by the disappearance of the C3a'-46 kDa band), under the same conditions, but in presence of 0.1 µM mini-FH, ~60% of C3b molecules are processed to iC3b$_2$ and 40% are inactivated to iC3b$_1$ (as judged by the relative ratio of C3a'-43 kDa and C3a'-46 kDa bands). (C) AP-ELISA-assay. AP-activation takes also place on the plastic surface in absence of LPS, however when LPS is present activation is much enhanced. AP-activation is most efficiently inhibited by mini-FH, followed by FH, CP30 and FH1-4. Single points were measured in triplicates and the average and associated standard deviation is shown for those. (E) In a CP-activation ELSA (ova-anti-ova) only compstatin CP30 blocks activation considerably. Each ELISA represents one typical result of three independently performed assays.

Next, FH and mini-FH were probed for their ability to act as a cofactor for factor I mediated proteolytic inactivation of fluid phase C3b into iC3b. Both analytes exhibited cofactor-activity; FH facilitates a somewhat faster consecutive cleavage of the first two scissile bonds (between residues 1303-1304 and 1320-1321) of the α-chain of C3b when compared to mini-FH (FIG. 5B). However, both $iC3b_1$ and $iC3b_2$ have been reported incapable of forming AP convertases and therefore inactive for further C3b-amplification.

To determine the complement regulatory activity in an ELISA assay, LPS was used as activating agent. Addition of mini-FH to a final concentration of 0.04 μM inhibited AP-activation by 50% (FIG. 5C). To achieve the same level of inhibition with addition of plasma purified FH, the serum dilution had to be supplemented with FH to a concentration of 0.53 μM—more than tenfold the amount needed of mini-FH. Addition of even higher amounts of compstatin analog CP30 ($^{(nMe)}$Gly-Ile-[Cys-Val-$^{(lMe)}$Trp-Gln-Asp-Trp-$^{(nMe)}$Gly-Ala-His-Arg-Cys]-$^{(nMe)}$Ile-NH$_2$ (SEQ ID NO:3), to a concentration of 0.7 μM, or FH1-4, to a concentration of 1.2 μM, also yielded 50% inhibition. Negative control analytes (FH19-20, FH12-13, linearized-scrambled compstatin (lin-scr-CP30)) showed no complement regulatory activity.

To probe the pathway specificity all analytes were also submitted to a CP-specific complement activation ELISA. Analytes were added to a 1:80 serum dilution in PBS++ (phosphate-buffered saline containing 5 mM $MgCl_2$ and 0.9 mM $CaCl_2$. At the concentration range tested, only the compstatin analog CP30 achieved inhibition of CP-activation. At a concentration of 0.13 μM, CP30 inhibited half of the CP-activation in this assay. Towards higher concentrations (6-8 μM) mild attenuation of CP-activation was also noticeable for mini-FH and to a lesser extent also for FH.

Mini-FH has Higher Protective Activity than FH in PNH Hemolytic Assays.

Next we evaluated AP-regulation in a physiological setting on a cell surfaces in a hemolytic assay, which mimics the PNH disease condition.

PNH phenotype was induced in healthy erythrocytes prior to exposing them to acidified serum that had been substituted with various analytes (according to Ezzell et al., 1991, supra). Brisk activation of the AP in acidified serum renders PNH erythrocytes, in contrast to healthy erythrocytes, susceptible to lysis by complement. Addition of the controls lin-scr-CP30 and FH12-13, which are void of any complement regulatory-function, produced the same levels of lysis as addition of PBS alone (FIG. 6A). Increasing concentrations of FH19-20 gradually increased lysis of erythrocytes and at a concentration of 2 μM reached the level of total lysis. Addition of CP30, FH1-4, FH and mini-FH resulted in dose-dependent AP-control and therefore in protection of PNH-induced RBCs from complement-mediated lysis. To reach 50% inhibition of lysis, analytes had to be added to a final concentration of 1.4 μM for CP30, 0.35 μM for FH1-4, 0.2 μM for purified FH or 0.02 μM for mini-FH. It is noted that the 52%-serum reactions naturally contained serum-FH at a concentration of about 1.6 μM (normal FH concentration in plasma is 3.2 μM) prior to addition of any analytes.

To analyze the contribution of polyanionic surface markers in conferring complement protection to RBCs of PNH-phenotype, the negatively charged sialic acid, which is abundant on erythrocyte surfaces, was removed enzymatically with neuraminidase (ND). Only analytes that contained the host-surface recognition domain CCP 20 of FH showed a differential protection behavior (FIG. 6B), which is consistent with a distinct reduction in their ability to recruit soluble complement regulators onto their surfaces. The ability of FH 19-20 to increase lysis of PNH-induced RBCs was abolished when sialic acid groups were removed from those RBCs, resulting in a level of lysis comparable to the mere addition of PBS.

The dose-dependent protection of vulnerable PNH-induced erythrocytes was confirmed when the same analytes were tested on erythrocytes derived from PNH-patients (FIG. 6C). Mini-FH inhibited lysis of PNH erythrocytes at an $EC_{50}$ of approximately 0.02-0.05 μM.

The present invention is not limited to the embodiments described and exemplified above, but is capable of variation and modification within the scope of the appended claims.

What is claimed:

1. A complement regulator comprising a complement regulating region that includes a plurality of complement control proteins (CCPs), linked by a flexible linker to a multifunctional binding region that enables binding of the complement regulator to (a) one or more C3b activation/inactivation products, (b) one or more oxidation end products and (c) one or more polyanionic surface markers on host cells, and wherein the flexible linker is of the same length and flexibility as a poly-Gly peptide at least 9, 10, 11 or 12 residues in length.

2. The complement regulator of claim 1, wherein the CCPs are derived from factor H.

3. The complement regulator of claim 2, wherein the CCPs are derived from SCRs 1-4 of factor H.

4. The complement regulator of claim 1, wherein the C3b activation/inactivation products contain thioester domains (TEDs).

5. The complement regulator of claim 4, wherein the C3b activation/inactivation products are C3b, iC3b, C3dg or C3d.

6. The complement regulator of claim 1, wherein the polyanionic surface markers on host cells are N-linked glycosyl units with sialic acid end-groups or glycosaminoglycans (GAGs) selected from heparin, heparan sulfate, chondroitin sulfate, dermantan sulfate, keratan sulfate and hyaluronan.

7. The complement regulator of claim 1, wherein the oxidation end products are malondialdehyde (MDA), 4-hydroxynonenal (4-HNE), carboxyethylpyrrole (CEP), oxidized phosphatidylserine (OxPS), oxidized cardiolipin (OxCL) and phosphocholine (PC).

8. The complement regulator of claim 1, wherein the multifunctional binding region is derived from SCRs 19 and 20 of factor H.

9. The complement regulator of claim 1, wherein the linker is of the same length and flexibility as a poly-Gly peptide at least 10, 11 or 12 residues in length.

10. The complement regulator of claim 9, wherein the linker is a poly-Gly peptide at least 12 residues in length.

11. The complement regulator of claim 1, comprising, from N- to C-terminus, SCRs 1-4 of factor H, a poly-Gly linker at least 12 residues in length, and SCRs 19-20 of factor H.

12. The complement regulator of claim 11, wherein the factor H is human factor H.

13. The complement regulator of claim 1, comprising a polypeptide that is functionally equivalent to SEQ ID NO:2.

14. The complement regulator of claim 13, wherein the polypeptide sequence has more than 90% sequence identity to that of SEQ ID NO:2.

15. The complement regulator of claim 14, comprising SEQ ID NO:2.

16. A polypeptide comprising, from N- to C-terminus, SCRs 1-4 of factor H, a poly-Gly linker at least 12 residues in length, and SCRs 19-20 of factor H.

17. The polypeptide of claim 16, wherein the factor H is human factor H.

18. The polypeptide of claim 17, comprising SEQ ID NO:2.

19. A pharmaceutical composition comprising the complement regulator of claim 1 and a pharmaceutically acceptable carrier.

* * * * *

UNITED STATES PATENT AND TRADEMARK OFFICE
CERTIFICATE OF CORRECTION

PATENT NO.        : 9,540,626 B2                                    Page 1 of 1
APPLICATION NO. : 14/386043
DATED             : January 10, 2017
INVENTOR(S)       : Lambris et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 72 days.

Signed and Sealed this
Twenty-fifth Day of September, 2018

Andrei Iancu
*Director of the United States Patent and Trademark Office*